US007485315B2

(12) United States Patent
Guiramand et al.

(10) Patent No.: US 7,485,315 B2
(45) Date of Patent: Feb. 3, 2009

(54) COMPOSITIONS COMPRISING A COMPOUND OF LOW SOLUBILITY AND A LIPOPHILIC AMINO ACID DERIVATIVE, USES THEREOF AND PROCESS FOR DISSOLVING A COMPOUND OF LOW SOLUBILITY

(75) Inventors: Carole Guiramand, Jouy en Josas (FR); Dominique Caplain, Paris (FR); Véronique Chevalier, Villecresnes (FR); Jean-Thierry Simonnet, Paris (FR); Pascal Richart, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/179,231

(22) Filed: Jun. 26, 2002

(65) Prior Publication Data

US 2003/0027864 A1 Feb. 6, 2003

(30) Foreign Application Priority Data

| | | |
|---|---|---|
| Jun. 26, 2001 | (FR) | 01 08428 |
| Jun. 26, 2001 | (FR) | 01 08429 |
| Jun. 26, 2001 | (FR) | 01 08430 |
| Jun. 26, 2001 | (FR) | 01 08431 |

(51) Int. Cl.
*A61K 8/02* (2006.01)
*A61K 31/19* (2006.01)
*A61K 31/16* (2006.01)

(52) U.S. Cl. .................... 424/401; 424/78.02; 514/506; 514/553; 514/557; 514/568; 514/613

(58) Field of Classification Search ................. 424/401, 424/78.02, 78.03; 514/506, 553, 555, 557, 514/568

See application file for complete search history.

(56) References Cited

U.S. PATENT DOCUMENTS

| | | | | |
|---|---|---|---|---|
| 5,262,407 | A * | 11/1993 | Leveque et al. | 514/139 |
| 5,736,537 | A | 4/1998 | Gubernick et al. | |
| 6,528,068 | B1 * | 3/2003 | Yumioka et al. | 424/401 |

FOREIGN PATENT DOCUMENTS

| | | |
|---|---|---|
| EP | 0336812 | 10/1989 |
| EP | 0378936 | 7/1990 |
| EP | 0662318 | 7/1995 |
| EP | 0 928 608 A2 | 7/1999 |
| EP | 1002536 | 5/2000 |
| EP | 1092422 | 4/2001 |
| FR | 2802416 | 6/2001 |
| WO | 99/10318 | 3/1999 |
| WO | 99/13857 | 3/1999 |
| WO | 01/26618 A2 | 4/2001 |

* cited by examiner

*Primary Examiner*—Sreeni Padmanabhan
*Assistant Examiner*—Shobha Kantamneni
(74) *Attorney, Agent, or Firm*—Nixon & Vanderhye P.C.

(57) ABSTRACT

The invention relates to a process for dissolving at least one compound of low solubility in water, the said process comprising the essential step of mixing the compound of low solubility with at least one lipophilic amino acid derivative. The invention also relates to a cosmetic or dermatological composition comprising, in a physiologically acceptable medium, at least one compound of low solubility and at least one lipophilic amino acid derivative. Among the compounds of low solubility that are especially included are aminophenol derivatives, salicylic acid derivatives, 2-amino-4-alkylaminopyrimidine 3-oxide derivatives and DHEA, and also its chemical or metabolic derivatives and precursors.

8 Claims, No Drawings

COMPOSITIONS COMPRISING A COMPOUND OF LOW SOLUBILITY AND A LIPOPHILIC AMINO ACID DERIVATIVE, USES THEREOF AND PROCESS FOR DISSOLVING A COMPOUND OF LOW SOLUBILITY

The present invention relates to compositions based on lipophilic amino acid derivatives, to uses thereof and to a process for dissolving at least one compound of low water-solubility.

It is known practice to use active agents in cosmetic and/or dermatological compositions, for example to care for, treat or provide beneficial effects to the skin. However, the use of some of these active agents poses a problem in that they are in crystalline form and are sparingly soluble or insoluble in water.

Thus, if they are introduced in unmodified form into cosmetic and/or dermatological compositions, they remain in the form of crystals, making the use of the composition containing them ineffective for treating the skin.

Generally, and for some of them, it is possible to introduce them in aqueous-alcoholic (water/ethanol) form, but the presence of alcohol is not always desirable, especially during application to certain areas of the face, such as around the eyes.

There is thus still a need to be able to introduce compounds of low solubility into cosmetic and/or dermatological compositions, especially into the aqueous phase of such compositions.

The expression "of low solubility" means herein compounds such that $\delta a>6\ J^{1/2}\ cm^{-3/2}$ and having a solubility in water at 25° C. of less than 1% by weight. A molecule is generally defined as being insoluble in water at and below a certain percentage (in this case 1%) when, macroscopically, a precipitate appears or when the solution becomes cloudy, and when, microscopically, crystals appear.

As recalled in the book "Properties of Polymers" by D. W. Van Krevelen, 3rd edition (Elsevier, 1990), page 200 et seq., the solubility of a compound in a given solvent is mainly determined by its chemical structure.

The solubility parameter allows a molecule to be defined with regard to the forces of interaction in which it participates.

This "Hansen" solubility parameter is obtained by the following equation:

$$\delta^2=\delta_d^2+\delta_p^2+\delta_h^2$$

in which:

$\delta_d$ represents the dispersion forces at the time of impact, known as the London forces or Van der Waals forces arising from the formation of dipoles induced during molecular impacts:

$$\delta_d=\Sigma F_d/V,$$

$\delta_p$ represents the molecular polarization forces or Debye interaction forces, i.e. the permanent dipole generated by the molecular considered when it is in solution; this is calculated by:

$$\delta_p=(\Sigma F_p^2/V)^{1/2}/V,$$

and $\delta_h$ represents the forces of specific interaction, for instance hydrogen bonding, acid/base bonding and donor/acceptor bonding, calculated by:

$$\delta_h=(\Sigma F_h/V)^{1/2}.$$

The parameters $\delta_d$, $\delta_p$ and $\delta_h$ are expressed in $(J/cm^3)^{1/2}$.

Each of the parameters $\delta_p$ and $\delta_h$ is non-zero when the molecule under consideration comprises at least one hetero atom.

$F_d$, $F_p$ and $F_h$ being the molar constants of the forces of interaction of groups of atoms constituting the molecules and V the molar volume, which may be determined by the Fedors method (Polymer Engineering and Science, February, 1974, Vol 14 No. 2), V being the sum of the molar volumes of the radicals of which the molecule under consideration is composed, the value V for most radicals is given in the Fedors article mentioned above.

To calculate the values of $F_d$, $F_p$ and $F_h$ for a given molecule, it suffices to calculate the sum of the contributions of the radicals of which the said molecule is composed. The values of $F_d$, $F_p$ and $F_h$ have been established for most radicals; the book "Properties of Polymers" by D. W. Van Krevelen mentioned above especially contains tables presenting these values for many radicals.

With the aim of obtaining an expression of the solubility as two components, the following has also been defined:

$$\delta_a^2=\delta_p^2+\delta_h^2=\delta^2-\delta_d^2$$

and as a result $\delta_a=(\delta_p^2+\delta_h^2)^{1/2}$

These notions of solubility and of cohesion are defined in particular in the book "Properties of Polymers" by D. W. Van Krevelen, 3rd edition (Elsevier, 1990), chapter 7, and in the article "A method for estimating both the solubility parameters and molar volumes of liquids" R. F. Fedors, Polymer Engineering and Science, February 1974 vol. 14 No. 2 pp. 147-154.

For the purposes of the present invention, the inventors have defined molecules of low solubility in water as being molecules having a solubility in water at 25° C. less than 1% by weight and such that $\delta a>6\ J^{1/2}\ cm^{-3/2}$.

It is often necessary to be able easily to dissolve in a physiologically acceptable medium molecules of low solubility in water. The solutions and compositions thus obtained are generally easy to use and they may be applied with a minimum of discomfort. In addition, it is often necessary to be able to dissolve a sufficient amount of these molecules of low solubility in order to use them cosmetically or dermatologically, without recrystallization of these molecules or loss of solubility of the composition containing them. The reason for that is that this instability would result in a loss of efficacy, to a greater or lesser extent, of these compositions and/or a change in their appearance, which would run the risk of discouraging the user from using them.

The Applicant has now discovered that lipophilic amino acid derivatives can, unexpectedly, increase the dissolution of these molecules of low solubility and keep these molecules dissolved in compositions that are, as a result, stable.

One subject of the present invention is thus a process for dissolving at least one compound of low solubility, the said process comprising the essential step of mixing the compound of low solubility with at least one lipophilic amino acid derivative, and also a composition comprising, in a physiologically acceptable medium, at least one compound with a solubility in water at 25° C. less than 1% and such that $\delta a>6\ J^{1/2}\ cm^{-3/2}$ and at least one lipophilic amino acid derivative.

For the purposes of the present patent application, the expression "physiologically acceptable medium" means a medium that is compatible with the skin, including the scalp, mucous membranes, the eyes and/or the hair.

By way of illustration, the lipophilic amino acid derivatives used for the purposes of the present patent application allowed the dissolution of:

- more than 20% of aminophenol derivatives without recrystallization after three weeks at 25° C., more than 15% of salicylic acid derivatives without recrystallization after three weeks at 25° C.

about 4% of diosgenin or hecogenin acetate without recrystallization after 24 hours at 25° C.

In the case of an emulsification, the use of one of these lipophilic amino acid derivatives makes it possible to dispense with the limit traditionally imposed by the content of solubilizing agent, since the cosmeticity of these solubilizing agents is generally unacceptable. In the context of the present invention, the emulsions keep a very acceptable level of cosmeticity despite having large contents of solubilizing agent.

The lipophilic amino acid derivative used according to the invention is preferably an amino acid ester of formula:

$$R'_1(CO)N(R'_2)CH(R'_3)(CH_2)n(CO)OR'_4$$

in which:

n is an integer equal to 0, 1 or 2, $R'_1$ represents a linear or branched $C_5$ to $C_{21}$ alkyl or alkenyl radical, $R'_2$ represents a hydrogen atom or a $C_1$ to $C_3$ alkyl group, $R'_3$ represents a radical chosen from the group formed by a hydrogen atom, a methyl group, an ethyl group and a linear or branched $C_3$ or $C_4$ alkyl radical, $R'_4$ represents a linear or branched $C_1$ to $C_{10}$ alkyl or $C_2$ to $C_{10}$ alkenyl radical or a sterol residue.

Preferably, the group $R'_1(CO)$— is an acyl group of an acid chosen from the group formed by capric acid, lauric acid, myristic acid, palmitic acid, stearic acid, behenic acid, linoleic acid, linolenic acid, oleic acid, isostearic acid, 2-ethylhexanoic acid, coconut oil fatty acids and palm kernel oil fatty acids. These fatty acids may also contain a hydroxyl group. Even more preferably, it will be lauric acid.

The portion —$N(R'_2)CH(R'_3)$ $(CH_2)_n(CO)$— of the amino acid ester is preferably chosen from the following amino acids: glycine, alanine, valine, leucine, isoleucine, serine, threonine, proline, hydroxyproline, β-alanine, aminobutyric acid, aminocaproic acid, sarcosine, or N-methyl-β-alanine.

Even more preferably, it will be sarcosine.

The portion of the amino acid esters corresponding to the group $OR'_4$ may be obtained from alcohols chosen from the group formed by methanol, ethanol, propanol, isopropanol, butanol, tert-butanol, isobutanol, 3-methyl-1-butanol, 2-methyl-1-butanol, fusel oil, pentanol, hexanol, cyclohexanol, octanol, 2-ethylhexanol, decanol, lauryl alcohol, myristyl alcohol, cetyl alcohol, cetostearyl alcohol, stearyl alcohol, oleyl alcohol, behenyl alcohol, jojoba alcohol, 2-hexadecyl alcohol, 2-octyldodecanol and isostearyl alcohol.

These amino acid esters may be obtained in particular from natural sources of amino acids. In this case, the amino acids are derived from the hydrolysis of natural proteins from plants (oat, wheat, soybean, palm or coconut) and, in this case, necessarily lead to amino acid mixtures that must then be esterified and then N-acylated. The preparation of such amino acids is more particularly described in patent application FR 2 796 550, which is incorporated herein by reference.

The amino acid ester that is more particularly preferred for the use in the present invention is isopropyl N-lauroylsavcosinate of formula:

$$CH_3—(CH_2)_{10}CO—N(CH_3)—CH_2—COO—CH—(CH_3)_2$$

The amino acid esters preferably used for the purposes of the present invention, and also their synthesis, are described in patent applications EP 1 044 676 and EP 0 928 608 from the company Ajinomoto Co.

In general, the lipophilic amino acid derivative(s) represent(s) from 0.01% to 90% by weight, preferably from 0.1% to 50% by weight and even more preferably from 0.1% to 30% by weight relative to the total weight of the composition.

Among the compounds of low solubility in water for the purposes of the present invention, the ones that are especially included are aminophenol derivatives, salicylic acid derivatives, 2-amino-4-alkylaminopyrimidine 3-oxide derivatives, in particular 2-amino-4-dodecylaminopyrimidine 3-oxide, DHEA (dehydroepiandrosterone) and its chemical or metabolic derivatives and precursors.

In general, the compound of low solubility represents from 0.001% to 30% by weight and preferably from 0.05% to 15% by weight relative to the total weight of the composition.

In particular, a subject of the present patent application is a composition comprising, in a physiologically acceptable medium, at least one aminophenol derivative and at least one lipophilic amino acid derivative.

The aminophenol derivatives are more particularly the derivatives of formula (I):

(I)

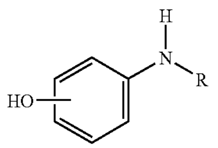

in which R is a radical chosen from the group formed by the radicals (a), (b) and (c)

(a) —CO—$NR_1R_2$ (b) —CO—O—$R_3$ (c) —$SO_2R_3$ in which $R_1$ represents a hydrogen atom or a linear or branched, saturated or unsaturated, optionally hydroxylated $C_1$ to $C_6$ alkyl radical, $R_2$ represents a hydrogen atom or a saturated or unsaturated, linear, cyclic or branched, optionally hydroxylated $C_1$ to $C_{30}$ alkyl radical, and $R_3$ represents a saturated or unsaturated, linear, cyclic or branched, optionally hydroxylated $C_1$ to $C_{30}$ alkyl radical.

In formula (I), among the linear or branched alkyl radicals $R_2$ or $R_3$ containing from 1 to 30 carbon atoms, mention may be made advantageously of methyl, ethyl, propyl, isopropyl, butyl, tert-butyl, hexyl, octyl, nonyl, 2-ethylhexyl, dodecyl, hexadecyl, behenyl, octadecyl and 2-butyloctyl radicals. Preferably, these radicals contain from 1 to 12 carbon atoms. Even more preferentially, the alkyl radical generally contains from 1 to 6 carbon atoms. Lower alkyl radicals that may be mentioned include methyl, ethyl, propyl, isopropyl, tert-butyl and hexyl radicals.

When it is unsaturated, a radical containing one or more ethylenic unsaturations is preferred, such as, more particularly, an allyl radical.

When the alkyl radical is cyclic, mention may be made especially of the cyclohexyl, cholesteryl or tert-butylcyclohexyl radical.

When it is hydroxylated, the radical preferably contains from 1 to 6 carbon atoms and from 1 to 5 hydroxyl groups. Among the monohydroxyalkyl radicals that are preferred is a radical preferably containing 1 or 3 carbon atoms, especially hydroxymethyl, 2-hydroxyethyl and 2- or 3-hydroxypropyl radicals.

Among the polyhydroxyalkyl radicals that are preferred are radicals containing from 3 to 6 carbon atoms and from 2 to 5 hydroxyl groups, such as 2,3-dihydroxypropyl, 2,3,4-trihydroxybutyl, 2,3,4,5-tetrahydroxypentyl and 2,3,4,5,6-pentahydroxyhexyl radicals.

The alkoxylated radicals are alkyl radicals, especially as described above, linked to an oxygen atom.

Preferably, the aminophenol derivatives used in the present patent application are those for which at least one and preferably all of the conditions below are satisfied:

the —OH function on the phenyl radical is in an ortho position or, advantageously, in the para position, R is chosen from a radical of formula (a) or (b).

Among the linear or branched alkyl radicals $R_1$ that may be mentioned are methyl, ethyl, propyl, isopropyl, tert-butyl and hexyl radicals.

The aminophenol derivative preferably used in the said composition is a para-aminophenol derivative and even more preferably it will be N-ethoxycarbonyl-4-para-aminophenol of formula (Ia):

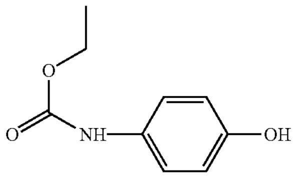

or N-cholesteryloxycarbonyl-4-para-aminophenol of formula (Ib):

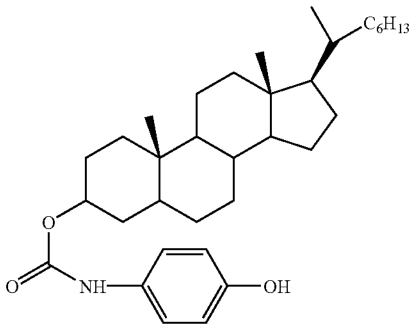

These aminophenol derivatives, and also the process for preparing them, are described in patent applications WO 99/10318 and WO 99/32077.

These derivatives contain a more of less long hydrocarbon, preferably alkoxycarbonyl, chain linked to the nitrogen atom. They have the drawback of being sparingly soluble or even totally insoluble in water. Their introduction into cosmetic compositions necessitates, for compounds with a short hydrocarbon chain, a dissolution in aqueous-alcoholic solution, which is not always desirable when the composition is intended, for example, to be applied around the eyes.

As regards compounds with a long hydrocarbon chain, they are insoluble in oils, on account of their steric bulk, and have a tendency to recrystallize in water.

The compositions according to the present invention comprising such an aminophenol derivative may be used as depigmenting or bleaching agents in a cosmetic and/or dermatological composition. Preferably, these compositions will be used for treating regional hyperpigmentations caused by melanocyte hyperactivity, such as idiopathic melasmas, occurring during pregnancy ("pregnancy mask" or chloasma) or during oestro-progestative contraception, localized hyperpigmentations caused by benign melanocyte hyperactivity and proliferation, such as senile pigmentary marks known as actinic lentigos, accidental hyperpigmentations or depigmentations, possibly caused by photosensitization or post-lesional cicatrization, and also certain leukodermas, such as vitiligo.

The concentration of aminophenol derivatives in the composition according to the present invention is between 0.001% and 30%, preferably between 0.001% and 15% and even more preferably between 0.1% and 5% by weight relative to the total weight of the composition. The amount of lipophilic amino acid derivatives and in particular of amino acid esters depends on the amount of aminophenol derivatives to be dissolved. It is generally between 0.01% and 90% by weight and preferably between 0.1% and 50% by weight relative to the total weight of the composition.

The physiologically acceptable medium for the composition of the invention preferably comprises at least one oil.

The composition comprising an aminophenol derivative according to the invention may be used as a cosmetic composition, in particular for depigmenting and/or bleaching human skin, head hair and/or other hairs, and for aesthetic enhancement.

The composition comprising an aminophenol derivative according to the present invention may also be used as a dermatological composition and more particularly as a dermatological composition for depigmenting and/or bleaching the skin, head hair and/or other hairs, especially for treating marks on the skin.

Thus, a subject of the invention is also the cosmetic use of the composition as defined above for depigmenting and/or bleaching the skin, head hair and/or other hairs, and a cosmetic treatment process for depigmenting and/or bleaching human skin, head hair and/or other hairs, which consists in applying to the skin, head hair and/or other hairs the aminophenol-based composition according to the invention. A subject of the invention is also the use of the composition as defined above for the manufacture of an ointment for depigmenting and/or bleaching the skin, head hair and/or other hairs and/or for removing marks.

The present invention also relates to a process for dissolving an aminophenol derivative of formula (I), comprising a step consisting in mixing this derivative with at least one lipophilic amino acid derivative, preferably an amino acid ester of formula (II). According to one preferred embodiment of the invention, the aminophenol derivative/lipophilic amino acid derivative ratio is between 0.001/99.999 and 30/70 and better still between 0.001/99.999 and 25/75.

For the purposes of the present patent application, the salicylic acid derivatives of low solubility are the derivatives for formula I' or monovalent or divalent salts or mixtures of these derivatives:

(I')

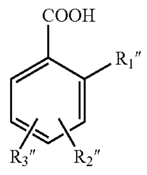

in which

R"$_1$ represents a hydroxyl radical or an ester of formula

—O—CO—R"$_4$ in which $R''_4$ is a saturated or unsaturated aliphatic radical containing from 1 to 26 carbon atoms and preferably from 1 to 18 carbon atoms, or an amine or thiol function optionally substituted with an alkyl radical containing from 1 to 18 carbon atoms and preferably from 1 to 12 carbon atoms, $R''_2$ and $R''_3$, independently of each other, are in one of the positions 3, 4, 5 or 6 on the benzene nucleus and represent, independently of each other, a hydrogen atom or a radical:

$$—(O)_n—(CO)_m—R''_5$$

in which n and m, independently of each other, are each an integer equal to 0 or 1, on condition that $R''_2$ and $R''_3$ are not simultaneously hydrogen atoms, and $R''_5$ represents a hydrogen, a saturated, linear, branched or cyclized aliphatic radical containing from 1 to 18 carbon atoms, an unsaturated radical containing from 3 to 18 carbon atoms, bearing one to nine conjugated or non-conjugated double bonds, the radicals possibly being substituted with at least one substituent chosen from halogen atoms (fluorine, chlorine, bromine or iodine), trifluoromethyl radicals, hydroxyl radicals in free form or esterified with an acid containing from 1 to 6 carbon atoms, or carboxyl radicals in free form or esterified with a lower alcohol containing from 1 to 6 carbon atoms, or an aromatic radical containing from 6 to 10 carbon atoms.

Preferably, the salicylic acid derivative is such that $R''_5$ represents a saturated aliphatic radical containing from 3 to 15 carbon atoms.

Preferably, the salicylic acid derivative is such that $R''_1$ represents a hydroxyl radical.

Preferably, the salicylic acid derivative is such that $R''_3$ is in position 5 of the benzene nucleus and $R''_2$ represents a hydrogen atom.

According to one preferred embodiment of the invention, the salicylic acid derivative is chosen from the 5-n-octanoylsalicylic, 5-n-decanoylsalicylic, 5-n-dodecanoylsalicylic, 5-n-octylsalicylic, 5-n-heptyloxy-salicylic, 4-n-heptyloxysalicylic, 5-tert-octyl-salicylic, 3-tert-butyl-5-methylsalicylic, 3-tert-butyl-6-methylsalicylic, 3,5-diisopropylsalicylic, 5-butoxysalicylic, 5-octyloxysalicylic, 5-propanoylsalicylic, 5-n-hexadecanoylsalicylic, 5-n-oleoyl-salicylic and 5-benzoylsalicylic derivatives, monovalent and divalent salts thereof, and mixtures thereof.

According to another preferred embodiment, the compositions comprise a salt of a salicylic acid derivative of formula I' chosen from strontium, calcium, magnesium, barium and manganese salts. Even more preferably, this salt of a salicylic acid derivative is chosen from the strontium salt of 5-octanoylsalicylic acid, the calcium salt of 5-octanoylsalicylic acid and the magnesium salt of 5-octanoylsalicylic acid, and mixtures thereof.

These derivatives are known in the prior art; in particular, patent application EP 662 318 relates to the use of such salicylic acid derivatives to manufacture cosmetic and/or dermatological compositions for treating the body and the face, especially for treating acne and ageing of the skin. Patent applications EP 0 662 318 and EP 987 011 describe processes for preparing such salicylic acid derivatives.

Salicylic acid derivatives are of great interest especially for preventing or repairing the main manifestations of ageing of the skin, i.e. wrinkles and fine lines, disorganization of the "grain" of the skin, modification of the complexion of the skin and the loss of firmness and tonicity of the skin. However, the use of these derivatives poses a problem in that, when they are introduced in unmodified form into topical compositions, they do not dissolve but remain in the form of crystals, thus making the use of the composition containing them ineffective for treating the skin.

In general, these derivatives are dissolved in lower alcohols, for instance ethanol or isopropanol, or solvents such as octyldodecanol, certain glycols or short-chain (less than C12) fatty alcohols. However, these lower alcohols have the drawback of drying out and irritating the skin: it is thus preferred to avoid using them in care products for the body and/or the face. In addition, these solubilizing agents can only be introduced in small amounts otherwise they run the risk of adversely affecting the cosmetic qualities (drying-out of the skin) and stability of the compositions containing them.

The concentration of salicylic acid derivatives in the composition according to the present invention is between 0.001% and 15% by weight and preferably between 0.1% and 5% by weight relative to the total weight of the composition. The amount of amino acid esters will depend on the amount of salicylic acid derivatives to be dissolved. It may be between 0.01% and 90% by weight and preferably between 0.1% and 50% by weight relative to the total weight of the composition.

The composition according to the invention comprising at least one salicylic derivative may be used as a cosmetic or dermatological composition, and especially for caring for, protecting, cleansing and/or making up human keratin materials (skin, lips or keratin fibres such as hair and eyelashes), and especially for combating the signs of ageing of the skin and/or for smoothing out facial and/or body skin and/or for treating the wrinkles and fine lines of the skin and/or for stimulating the process of epidermal renewal and/or for depigmenting and bleaching the skin and/or for treating acne and/or for treating skin disorders.

The expression "skin disorders" in particular means zona, burns, eczema, demodecia, skin ulcers, fibrosis, the control of cicatrizations, psoriasis, pruritus, dermatitis, ichthyosis, corns and verrucas.

Thus, a subject of the invention is also the cosmetic use of the cosmetic composition as defined above for protecting, caring for, cleansing and/or making up the skin and/or mucous membranes and/or keratin fibres.

A subject of the invention is also a cosmetic treatment process for protecting, caring for, cleansing and/or making up the skin and/or mucous membranes and/or keratin fibres, which consists in applying the composition according to the invention to the skin and/or mucous membranes and/or keratin fibres.

A subject of the invention is also a cosmetic treatment process for combating the signs of ageing of the skin and/or for improving the radiance of the complexion and/or for making facial and/or body skin smooth and/or for treating wrinkles and fine lines of the skin and/or for stimulating the process of epidermal renewal and/or for depigmenting and/or bleaching the skin, which consists in applying to the skin the composition containing a salicylic acid derivative according to the invention.

A subject of the invention is also the use of the composition according to the invention for the manufacture of a dermatological composition for combating the signs of ageing of the skin and/or for combating acne and/or for combating skin disorders.

The present invention also relates to a process for dissolving at least one salicylic derivative of formula I' with a lipophilic amino acid derivative. The lipophilic amino acid derivative is preferably chosen from an amino acid ester of formula (II) indicated above.

The salicylic acid derivative/amino acid ester weight ratio is preferably from 0.001/99.999 to 35/65 and preferably from 0.1/99.9 to 30/70.

The derivatives of the 2-amino-4-alkylaminopyrimidine 3-oxide family are the derivatives of general formula

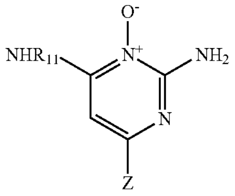

in which $R_{11}$ represents an alkyl group containing from 1 to 20 carbon atoms and Z represents a hydrogen atom or a radical —$OR_{12}$ in which $R_{12}$ represents an alkyl group containing from 1 to 12 carbon atoms, and also the acylated forms thereof or the addition salts thereof with acids.

Preferably, $R_{11}$ is chosen from the group formed by hexyl, heptyl, octyl, nonyl, decyl, undecyl and dodecyl radicals.

Preferably, $R_{12}$ is chosen from the group formed by ethyl, propyl, butyl, pentyl and hexyl radicals.

More preferably, it is 2-amino-4-dodecylaminopyrimidine 3-oxide.

The derivatives of the 2-amino-4-alkylaminopyrimidine 3-oxide family may be used especially in or for the preparation of a cosmetic or dermatological composition in accordance with the present invention to prevent and treat problems associated with sensitive skin and skin disturbances such as skin discomfort, tautness of the skin, skin itching, skin swelling, skin redness and the sensation of hot skin.

Another family of molecules that comes within the definition of molecules of low solubility in water comprises DHEA-based compounds. Among the DHEA-based compounds that are included are DHEA, its derivatives, its chemical or biological precursors and its metabolic derivatives, and mixtures thereof.

DHEA (dehydroepiandrosterone) has the formula

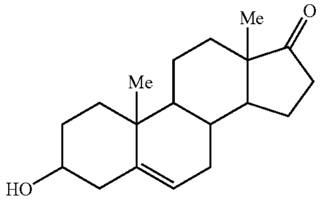

The expression "DHEA precursors" concerned by the invention means its biological precursors that may be converted into DHEA during metabolism, and also its chemical precursors that may be converted into DHEA by exogenous chemical reaction.

Examples of biological precursors are Δ5-pregnenolone, 17α-hydroxypregnenolone and 17α-hydroxypregnenolone sulphate, this list not intended to be limiting.

The expression "chemical precursors of DHEA" especially means sapogenins and derivatives thereof such as hecogenin (3β, 5α-23R)-3-hydroxyspirostan-12-one) and hecogenin acetate, diosgenin (5-spirostene-3β-ol), smilagenin and sarsapogenin, and also natural extracts containing them, in particular fenugreek and extracts of Dioscorea plants such as extract of wild yam, this list not intended to be limiting.

The expression "DHEA derivatives" means both its metabolic derivatives and its chemical derivatives. Metabolic derivatives that may especially be mentioned include Δ5-androstene-3,17-diol and especially 5-androstene-3β,17β-diol, Δ4=androstene-3,17-dione, 7-hydroxy-DHEA (7α-hydroxy-DHEA or 7β-hydroxy-DHEA) and 7-keto-DHEA which is itself a metabolite of 7β-hydroxy-DHEA, this list not intended to be limiting.

7α-hydroxy-DHEA is, with 5-androstene-3β,17β-diol, a major metabolite of DHEA, obtained by the action of 7α-hydroxylase on DHEA. 7β-Hydroxy-DHEA is a minor metabolite of DHEA, obtained by the action of 7β-hydroxylase on DHEA.

The 7-hydroxy-DHEA preferably used in the compositions according to the present invention is 7α-hydroxy-DHEA. A process for preparing this compound is described in patent applications FR 2 771 105 and WO 94/08588.

Chemical derivatives of DHEA that may also be mentioned include DHEA salts and in particular water-soluble salts such as DHEA sulphate; DHEA esters such as hydroxycarboxylic acid esters of DHEA, in particular those described in patent U.S. Pat. No. 2,736,537 or DHEA salicylate, DHEA acetate, DHEA valerate (or n-heptanoate) and DHEA enanthate.

Mention may also be made of DHEA carbamates, DHEA 2-hydroxymalonate esters and DHEA amino acid esters. Finally, mention may be made of 3β-acetoxy-7-oxo-DEHA, which may specially be prepared as described in patents U.S. Pat. Nos. 5,869,709 and 6,111,118. Obviously, this list is not limiting.

The concentration of DHEA-based compounds in the composition according to the present invention may advantageously range from 0.001% to 30% by weight, preferably from 0.01% to 20% and even more preferably from 0.01% to 10% by weight relative to the total weight of the composition. These compounds will be in solubilized form between 20° C. and 90° C.

The lipophilic amino acid derivative represents from 0.1% to 80% by weight and preferably from 1% to 50% by weight relative to the total weight of the composition. This derivative may be used alone or with other oils that are solvents or non-solvents for the DHEA-based compound.

DHEA and its chemical or metabolic derivatives and precursors may especially be used in or for the preparation of a cosmetic or dermatological composition in accordance with the present invention for preventing and treating problems associated with chronological or actinic ageing and in particular for reviving the radiance and fortifying the structure of the skin and integuments (eyelashes, nails, head hair and other hairs).

The composition of the invention, in a physiologically acceptable medium, may be used as a composition, especially a cosmetic or dermatological composition, for preventing and/or treating problems associated with chronological or actinic ageing.

A subject of the invention is thus the cosmetic use of the cosmetic composition as defined above, for preventing and treating problems associated with the chronological or actinic ageing of keratin materials (skin, mucous membranes and integuments) and especially the skin.

A subject of the invention is also a cosmetic process for treating keratin materials, and especially the skin, to prevent and/or treat problems associated with chronological or actinic ageing, which consists in applying the composition according to the invention to these keratin materials.

A subject of the invention is also the use of the composition according to the invention for preventing and/or treating problems associated with the chronological or actinic ageing of keratin materials and especially the skin, and also the use of the composition according to the invention for the manufacture of a dermatological composition for preventing and/or treating problems associated with the chronological or actinic ageing of keratin materials.

A subject of the present invention is also a process for dissolving a DHEA-based compound, such that this compound is mixed with a lipophilic amino acid derivative, the DHEA derivative/lipophilic amino acid derivative weight ratio is preferably between 1:1 000 and 1:2 and preferentially from 1:500 to 1:5. Preferably, the lipophilic amino acid derivative is an amino acid ester of formula (I).

The composition according to the present invention may be in any form normally used in cosmetics that is compatible with the use of DHEA and its derivatives, precursors and metabolites, or mixtures thereof.

A subject of the present patent application is also the composition containing at least one derivative of low solubility as a cosmetic composition and the cosmetic use of the cosmetic composition according to the present invention.

A subject of the present patent application is also the cosmetic use of the composition for protecting, caring for, cleansing and/or making up the skin, mucous membranes and/or keratin fibres.

A subject of the patent application is also a cosmetic treatment process for protecting, caring for, cleansing and/or making up the skin and/or mucous membranes and/or keratin fibres, which consists in applying the composition according to the invention to the skin and/or mucous membranes and/or keratin fibres.

A subject of the present patent application is also a solubilization process in which the compound of low solubility/lipophilic amino acid derivative ratio is between 0.001% and 50%, preferably between 1% and 40% and more preferably between 1% and 20%.

A subject of the present patent application is also the use of the composition according to the invention for the manufacture of a dermatological composition.

The cosmetic composition according to the invention may be in the forms normally used in cosmetics.

It may be in any form normally used for topical application, especially in the form of an aqueous-alcoholic solution, an oil-in-water or water-in-oil or multiple emulsion, an oily gel or a liquid, pasty or solid anhydrous product, or in the form of a dispersion in the presence of spherules, these spherules possibly being polymer nanoparticles such as nanospheres or nanocapsules or lipid vesicles of ionic or nonionic type. These compositions are prepared according to the usual methods.

This composition may be more or less fluid and may have the appearance of a white or coloured cream, an ointment, a milk, a lotion, a serum, a paste or a mousse. It may optionally be applied to the skin or the hair in the form of an aerosol. It may also be in solid form, and for example in the form of a stick.

In a known manner, the cosmetic and dermatological compositions according to the invention may also contain adjuvants that are common in cosmetics and dermatology, such as hydrophilic or lipophilic gelling agents, hydrophilic or lipophilic active agents, preserving agents, antioxidants, solvents, fragrances, fibres, fillers, screening agents, pigments, odour absorbers and dyestuffs. The amounts of these various adjuvants are those conventionally used in the fields under consideration, and for example from 0.01% to 50% relative to the total weight of the composition. Depending on their nature, these adjuvants may be introduced into the fatty phase, into the aqueous phase, into lipid vesicles and/or into nanoparticles.

Needless to say, a person skilled in the art will take care to select these optional additional active or non-active compounds, and/or the amount thereof, such that the advantageous properties of the derivatives of low solubility are not, or are not substantially, adversely affected by the envisaged addition.

When the composition according to the invention is an emulsion, the proportion of the fatty phase can range from 0.5% to 80% by weight and preferably from 5% to 50% by weight relative to the total weight of the composition. The oils, emulsifiers and co-emulsifiers used in the composition in emulsion form are chosen from those conventionally used in the field under consideration.

The fatty phase or oily phase usually contains at least one oil. As oils that may be used in the composition of the invention, examples that may be mentioned include:

hydrocarbon-based oils of animal origin, such as perhydrosqualene;

hydrocarbon-based oils of plant origin, such as liquid triglycerides of fatty acids containing from 4 to 10 carbon atoms, for instance heptanoic or octanoic acid triglycerides or alternatively, for example, sunflower oil, corn oil, soybean oil, marrow oil, grapeseed oil, sesame oil, hazelnut oil, apricot oil, macadamia oil, arara oil, sunflower oil, castor oil, avocado oil, caprylic/capric acid triglycerides, for instance those sold by the company Stearineries Dubois or those sold under the names Miglyol 810, 812 and 818 by the company Dynamit Nobel, jojoba oil or karite butter oil;

synthetic esters and synthetic ethers, especially of fatty acids, for instance oils of formulae $R^6COOR^7$ and $R^6OR^7$ in which $R^6$ represents a fatty acid residue containing from 8 to 29 carbon atoms and $R^7$ represents a branched or unbranched hydrocarbon-based chain containing from 3 to 30 carbon atoms, such as, for example, purcellin oil, isononyl isononanoate, isopropyl myristate, 2-ethylhexyl palmitate, 2-octyl-dodecyl stearate, 2-octyldodecyl erucate or isostearyl isostearate; hydroxylated esters such as isostearyl lactate, octyl hydroxystearate, octyldodecyl hydroxystearate, diisostearyl malate, triisocetyl citrate and fatty alkyl heptanoates, octanoates and decanoates; polyol esters, for instance propylene glycol dioctanoate, neopentyl glycol diheptanoate and diethylene glycol diiso-nonanoate; and pentaerythritol esters, for instance pentaerythrityl tetraisostearate;

linear or branched hydrocarbons of mineral or synthetic origin, such as volatile or non-volatile liquid paraffins, and derivatives thereof, petroleum jelly, polydecenes, and hydrogenated polyisobutene such as parleam oil;

fatty alcohols containing from 8 to 26 carbon atoms, for instance cetyl alcohol, stearyl alcohol and a mixture thereof (cetylstearyl alcohol), octyldodecanol, 2-butyloctanol, 2-hexyldecanol, 2-undecylpentadecanol, oleyl alcohol or linoleyl alcohol;

alkoxylated and especially ethoxylated fatty alcohols such as oleth-12;

partially hydrocarbon-based and/or silicone-based fluoro oils, for instance those described in document JP-A-2 295 912. Examples of fluoro oils which may also be mentioned include perfluoromethylcyclopentane and perfluoro-1,3-dimethylcyclohexane, sold under the names “Flutec PC1®”, and “Flutec PC3®” by the company BNFL Fluorochemicals; perfluoro-1,2-dimethylcyclobutane; perfluoroalkanes such as dodecafluoropentane and tetradecafluorohexane, sold under the names “PF 5050®” and “PF 5060®” by the company 3M, or alternatively bromoperfluorooctyl sold under the name “Foralkyl®” by the company Atochem; nonafluoromethoxybutane sold under the name “MSX 4518®”, by the company 3M and nonafluoroethoxyisobutane; perfluoromorpholine derivatives, such as the 4-trifluoromethylperfluoromorpholine sold under the name “PF 5052®” by the company 3M;

silicone oils, for instance volatile or non-volatile polymethylsiloxanes (PDMSs) containing a linear or cyclic silicone chain, that are liquid or pasty at room temperature, especially cyclopolydimethylsiloxanes (cyclomethicones) such as cyclohexasiloxane; polydimethylsiloxanes comprising alkyl, alkoxy or phenyl groups, that are pendent or at the end of a silicone chain, these groups containing from 2 to 24 carbon atoms; phenylsilicones, for instance phenyltrimethicones, phenyldimethicones, phenyltrimethylsiloxydiphenylsiloxanes, diphenyldimethicones, diphenylmethyldiphenyltrisiloxanes, 2-phenylethyltrimethylsiloxysilicates and polymethylphenylsiloxanes; and mixtures thereof.

In the list of oils mentioned above, the expression “hydrocarbon-based oil” means any oil mainly comprising carbon and hydrogen atoms, and optionally ester, ether, fluoro, carboxylic acid and/or alcohol groups.

The other fatty substances that may be present in the oily phase are, for example, fatty acids containing from 8 to 30 carbon atoms, for instance stearic acid, lauric acid, palmitic acid and oleic acid; waxes, for instance lanolin, beeswax, carnauba wax or candelilla wax, paraffin waxes, lignite wax or microcrystalline waxes, ceresin or ozokerite, synthetic waxes such as polyethylene waxes, Fischer-Tropsch waxes; gums such as silicone gums (dimethiconol); silicone resins such as trifluoromethyl-C1-4-alkyldimethicone and trifluoropropyldimethicone; and silicone elastomers, for instance the products sold under the names “KSG” by the company Shin-Etsu, under the names “Trefil”, “BY29” or “EPSX” by the company Dow Corning or under the names “Gransil” by the company Grant Industries.

These fatty substances may be chosen in a varied manner by a person skilled in the art so as to prepare a composition having the desired properties, for example in terms of consistency or texture. The emulsions may contain at least one emulsifier chosen from amphoteric, anionic, cationic and nonionic emulsifiers, used alone or as a mixture.

When the composition is an emulsion, it generally contains at least one emulsifier. The emulsifiers are chosen in an appropriate manner depending on the emulsion to be obtained: water-in-oil (W/O) or oil-in-water (O/W) emulsions.

For the O/W emulsions, examples of emulsifiers that may be used include a nonionic emulsifier, for instance saccharide esters and ethers such as sucrose stearate, sucrose cocoate and the mixture of sorbitan stearate and of sucrose cocoate sold by the company ICI under the name Arlatone 2121®; polyol esters, in particular glycerol or sorbitol esters, such as glyceryl stearate, polyglyceryl-2 stearate and sorbitan stearate; glycerol ethers; oxyethylenated and/or oxypropylenated ethers such as the oxyethylenated, oxypropylenated ether of lauryl alcohol containing 25 oxyethylene groups and 25 oxypropylene groups (CTFA name “PPG-25 laureth-25”) and the oxyethylenated ether of the mixture of $C_{12}$-$C_{15}$ fatty alcohols containing 7 oxyethylene groups (CTFA name “$C_{12}$-$C_{15}$ Pareth-7”); ethylene glycol polymers such as PEG-100, and mixtures thereof.

For the water-in-oil (W/O) emulsions, mention may be made, for example, as emulsifiers, of fatty esters of a polyol, in particular of glycerol or of sorbitol, and in particular polyol isostearates, oleates and ricinoleates, such as the mixture of petrolatum, of polyglyceryl-3 oleate and of glyceryl isostearate, hydrogenated castor oil and of ozokerite, sold under the name Protegin W® by the company Goldschmidt, sorbitan isostearate, polyglyceryl diisostearate, polyglyceryl-2 sesquiisostearate; saccharide esters and ethers such as “methyl glucose dioleate”; fatty esters such as magnesium lanolate; dimethicone copolyols and alkyldimethicone copolyols such as Laurylmethicone copolyol sold under the name Dow Corning 5200 Formulation Aid by the company Dow Corning and Cetyl dimethicone copolyol sold under the name Abil EM 90® by the company Goldschmidt, and mixtures thereof.

The emulsifiers may be introduced in their native form or in the form of mixtures with other emulsifiers and/or with other compounds such as fatty alcohols or oils.

Examples that may be mentioned of active agents that may be used in the composition of the invention include moisturizers, for example protein hydrolysates and polyols such as glycerol, glycols, for instance polyethylene glycols, and sugar derivatives; natural extracts; procyannidol oligomers; vitamins, for instance vitamin A (retinol), vitamin C (ascorbic acid), vitamin E (tocopherol), vitamin B5 (panthenol) and vitamin B3 (niacinamide); vitamin K urea; caffeine; depigmenting agents such as kojic acid and caffeic acid; salicylic acid (for those compositions which do not already contain a salicylic acid derivative); α-hydroxy acids such as lactic acid and glycolic acid; retinoids such as carotenoids; sunscreens, fillers, pigments, dyes, keratolytic agents, preserving agent, anti-oxidants, fragrances, hydrocortisone; melatonin; extracts of algae, fungi, plants, yeasts or bacteria; hydrolysed, partially hydrolysed or unhydrolysed proteins, and enzymes; antibacterial active agents for treating greasy skin, for instance 2,4,4'-trichloro-2'-hydroxydiphenyl ether (or triclosan) and 3,4,4'-trichlorocarbanilide (or triclocarban), as lazeleic acid and benzoylperoxide; matt-effect agents, for instance fibres; tensioning agents; optical brighteners; and mixtures thereof, such as, for example, a mixture of vitamins (for example A and C or A+C+E).

The active agent(s) may be present in a concentration ranging from 0.01% to 20%, preferably from 0.1% to 10% and better still from 0.5% to 5% relative to the total weight of the composition.

EXAMPLES

Molecules of low solubility in water for the purposes of the present invention are presented in the table below; they are sparingly soluble in water especially at room temperature and have a $\delta a > 6\ J^{1/2}\ cm^{-3/2}$.

| | Solubility in water at 25° C. | δa in $J^{1/2} \cdot cm^{-3/2}$ |
|---|---|---|
| N-ethoxycarbonyl-para-aminophenol | <1% | 16.1 |
| N-cholesteryloxy-carbonyl-para-aminophenol | | 8.7 |
| (3β, 5α, 25R)-3-hydroxyspirostan-12-one (hecogenin acetate) | | 6.7 |
| 5-spirostene-3-β-ol (diosgenin) | | 8.6 |

-continued

| | Solubility in water at 25° C. | δa in $J^{1/2} \cdot cm^{-3/2}$ |
|---|---|---|
| 5-n-octanoylsalicylic acid | | 11.3 |
| DHEA | | 9.9 |
| 2-amino-4-dodecyl-aminopyrimidine 3-oxide | | 8.9 |

The examples that follow illustrate the invention without limiting its scope.

1—Simple Solubility

Protocol: The derivatives of low solubility in water are weighed out and placed in a sealed pill bottle. The required amount of solvent is added. The suspension is stirred (magnetic stirring) at 80° C. for not more than 1 hour.

The dissolution or non-dissolution of the active agent and the change over time are reported in the table below.

The non-solubility of the active agent in the solvent is characterized macroscopically by a precipitate or just a cloudy solution, and microscopically by the presence of crystals.

The solvent used is isopropyl N-lauroylsarcosinate.

| Definition | Content | Solubilization at T0 | Stability over time at 25° C. |
|---|---|---|---|
| N-cholesteryloxy-carbonyl-para-aminophenol | 5%<br>9% | | clear for 7 days<br>clear for 4 days |
| N-ethoxycarbonyl-para-aminophenol | 5%<br>20%<br>23%<br>26% | no recrystal-lization | clear for 18 days<br>clear for 6 days<br>clear for 6 days<br>clear for 1 day |
| DHEA | 20% | no recrystal-lization | — |
| 2-amino-4-dodecyl-aminopyrimidine 3-oxide | 1% | no recrystal-lization | clear for 1 day |
| Diosgenin | 2% | no recrystal-lization | clear for 3 weeks |
| Hecogenin acetate | 2% | no recrystal-lization | clear for 1 day |
| 5-octanoyl-salicylic acid | 5%<br>9%<br>27% | no recrystal-lization | clear for 7 days<br>clear for 4 days<br>clear |

2—Emulsification

The dissolution of the active agents with the solvents (solubilizing agents) mentioned above was confirmed in emulsion, and thus makes it possible to formulate stable compositions.

The emulsions prepared are O/W emulsions, with Simulson 165 (mixture of glyceryl stearate and PEG-100 stearate) as surfactant.

The physicochemical stability of the emulsions is confirmed by macroscopic and microscopic monitoring, and monitoring of the pH and the viscosity, after 24 hours and over time. The composition according to the present invention may be in the forms normally used in cosmetics.

Examples of Compositions

| | | N-cholesteryl-oxycarbonyl-para-aminophenol | | N-ethoxy-carbonyl-para-aminophenol | | 5-n-octanoyl-salicylic acid | |
|---|---|---|---|---|---|---|---|
| PHASE | CTFA name | Example 1 in accordance with the invention | Comparative example 1 | Example 2 in accordance with the invention | Comparative example 2 | Example 3 in accordance with the invention | Comparative example 3 |
| A | Preserving agent | 0.2 | 0.2 | 0.2 | 0.2 | 0.2 | 0.2 |
| | Disodium EDTA | 0.15 | 0.15 | 0.15 | 0.15 | 0.15 | 0.15 |
| | Glycerol | 3 | 3 | 3 | 3 | 3 | 3 |
| | Water | qs 100 | qs 100 | qs 100 | qs 100 | qs 100 | qs 100 |
| B | Glyceryl stearate and PEG-100 stearate | 0.3 | 0.3 | 0.3 | 0.3 | 0.3 | 0.3 |
| | Cetyl alcohol | 0.4 | 0.4 | 0.4 | 0.4 | 0.4 | 0.4 |
| | Preserving agent | 0.1 | 0.1 | 0.1 | 0.1 | 0.1 | 0.1 |
| | Triclosan | 0.1 | 0.1 | 0.1 | 0.1 | 0.1 | 0.1 |
| C | N-cholesteryl-carbonyl-para-amino-phenol | 0.5 | 0.5 | — | — | — | — |
| | N-ethoxy-carbonyl-para-aminophenol | — | — | 2 | 2 | — | — |

-continued

| PHASE | CTFA name | N-cholesteryl-oxycarbonyl-para-aminophenol: Example 1 in accordance with the invention | N-cholesteryl-oxycarbonyl-para-aminophenol: Comparative example 1 | N-ethoxy-carbonyl-para-aminophenol: Example 2 in accordance with the invention | N-ethoxy-carbonyl-para-aminophenol: Comparative example 2 | 5-n-octanoyl-salicylic acid: Example 3 in accordance with the invention | 5-n-octanoyl-salicylic acid: Comparative example 3 |
|---|---|---|---|---|---|---|---|
| | 5-n-octanoylsalicylic acid | — | — | — | — | 1 | 1 |
| | Isopropyl lauroyl-sarcosinate | 10 | — | 10 | — | 10 | — |
| D | Crosslinked polymer (acrylates/$C_{10}$-$C_{30}$ alkyl acrylate) | 0.5 | 0.5 | 0.5 | 0.5 | 0.5 | 0.5 |
| | Cyclohexa-siloxane | 5 | 5 | 5 | 5 | 5 | 5 |
| E | Water | 10 | 10 | 10 | 10 | 10 | 10 |
| | Alcohol | 5 | 5 | 5 | 5 | 5 | 5 |
| F | Polyacryl-amide and $C_{13}$-$C_{14}$ isoparaffin and laureth-7 | 1 | 1 | 1 | 1 | 1 | 1 |
| G | Triethanol-amine | 1.03 | 1.03 | 1.03 | 1.03 | 1.03 | 1.03 |
| | Water | 7 | 7 | 7 | 7 | 7 | 7 |

Procedure

Phase A

The mixture is heated to 85° C. Stirring is carried out to dissolve the preserving agents. The temperature is then reduced to 75° C. to form the emulsion.

Phase B

The mixture is heated to 75° C. and homogenized until fully dissolved.

Preparation of the emulsion: B is poured into A at 75° C. with stirring for 15 minutes.

Phase C

The mixture is homogenized until fully dissolved at 30° C. and is added to the emulsion (A+B) at 60° C.

Phase D

The mixture is dispersed at room temperature and added to the emulsion (A+B+C) at 60° C. The resulting mixture is homogenized.

Phases E, F and G

These phases are prepared at room temperature and are then added to the emulsion (A+B+C+D) at 40° C., and the resulting mixture is homogenized with stirring. The emulsion is allowed to cool to 25° C.

It was shown that the dissolution of the derivatives of low solubility with amino acid esters may indeed be achieved in emulsion, so as to confirm that it is possible to formulate stable cosmetic compositions containing such derivatives.

The emulsions prepared above are oils in water with Simulsol 165 sold by the company SEPPIC as surfactant, Simulsol 165 being a mixture of glyceryl stearate and PEG-100 stearate.

The physicochemical stability of the emulsions is confirmed by macroscopic and microscopic monitoring, and monitoring of the pH and the viscosity, after 24 hours.

| | With 10% isopropyl N-lauroylsarcosinate (in accordance with the invention) | Without isopropyl N-lauroylsarcosinate |
|---|---|---|
| 0.5% N-cholesteryl-oxycarbonyl-para-aminophenol | Example 1 Emulsion without crystals, it remains in accordance with the invention for up to 2 months at 4/25 and 45° C. | Comparative example Fine emulsion with crystals from T 24 hours |
| 2% N-ethoxycarbonyl-para-aminophenol | Example 2 Emulsion without crystals, it remains in accordance with the invention for up to 2 months at 4/25 and 45° C. | Comparative example Fine emulsion with crystals from T 24 hours |
| 1% 5-N-octanoylsalicylic acid | Example 3 Emulsion without crystals, it remains in accordance with the invention for up to 2 months at 4/25 and 45° C. | Comparative example Fine emulsion with crystals from T 24 hours |

The compositions in accordance with the invention contain no crystals and are stable over time and with temperature, whereas the compositions of the comparative examples contain crystals within 24 hours of their preparation.

Example 3

Oil-in-water emulsion of oleosome type containing 1% DHEA.

| | | |
|---|---|---|
| Phase A | | |
| Glyceryl stearate | | 2.5% |
| PEG-8 stearate | | 2.5% |
| Stearic acid | | 1% |
| Preserving agent | | 0.1% |
| Isopropyl N-lauroyl sarcosinate | | 8% |
| Miglyol 812 | | 22% |
| DHEA | | 1% |
| Phase B | | |
| Triethanolamine | | 0.25% |
| Preserving agent | | 0.2% |
| Glycerol | | 5% |
| Distilled water | qs | 100% |
| Phase C | | |
| Carbomer | | 0.3% |
| Distilled water | | 14.95% |
| 10% sodium hydroxide in water | | 0.25% |

Procedure:

Phase A and phase B are brought to 75° C., separately. Phase B is introduced into phase A with stirring using a rotor-stator, for example a Moritz or Turrax blender. The temperature is also maintained. After stirring for about 30 minutes, the mixture is homogenized three times at high pressure, between 200 b and 900 b. The suspension is then cooled to room temperature, after which phase C is dispersed using a deflocculator. A white emulsion suitable for skincare is obtained, in which the DHEA does not recrystallize after at least one month at 4° C. Under the same conditions, in a composition containing 8% octyldodecanol instead of the 8% of isoproyl N-lauroyl sarcosinate, a start of recrystallization of the DHEA is noted.

Example 4

Oil-in-water emulsion of oleosome type containing 2% DHEA.

| | | |
|---|---|---|
| Phase A | | |
| Glyceryl stearate | | 2.5% |
| PEG-8 stearate | | 2.5% |
| Stearic acid | | 1% |
| Preserving agent | | 0.1% |
| Isopropyl N-lauroyl sarcosinate | | 25% |
| Miglyol 812 | | 5% |
| DHEA | | 2% |
| Phase B | | |
| Triethanolamine | | 0.25% |
| Preserving agent | | 0.2% |
| Glycerol | | 5% |
| Distilled water | qs | 100% |
| Phase C | | |
| Carbomer | | 0.3% |
| Distilled water | | 14.95% |
| Sodium hydroxide at 10% in water | | 0.25% |

The procedure is similar to that of Example 4, the only difference being that, for this type of composition, isopropyl N-lauroyl sarcosinate produces an emulsion containing 2% of dissolved DHEA.

Example 5

Oil-in-water emulsion of oleosome type containing 1% 7-keto-DHEA.

| | | |
|---|---|---|
| Phase A | | |
| Glyceryl stearate | | 2.5% |
| PEG-8 stearate | | 2.5% |
| Stearic acid | | 1% |
| Preserving agent | | 0.1% |
| isopropyl N-lauroyl sarcosinate | | 8% |
| Miglyol 812 | | 22% |
| 7-keto-DHEA | | 1% |
| Phase B | | |
| Triethanolamine | | 0.25% |
| Preserving agent | | 0.2% |
| Glycerol | | 5% |
| Distilled water | qs | 100% |
| Phase C | | |
| Carbomer | | 0.3% |
| Distilled water | | 14.95% |
| Sodium hydroxide at 10% in water | | 0.25% |

The procedure is the same as that of Example 4. When combined with 7-keto-DHEA, isopropyl N-lauroyl sarcosinate allows the 7-keto-DHEA to avoid recrystallizing.

Example 6

Oil-in-water emulsion of oleosome type containing 1% 7α-hydroxy-DHEA.

| | | |
|---|---|---|
| Phase A | | |
| Glyceryl stearate | | 2.5% |
| PEG-8 stearate | | 2.5% |
| Stearic acid | | 1% |
| Preserving agent | | 0.1% |
| Isopropyl N-lauroyl sarcosinate | | 8% |
| Miglyol 812 | | 22% |
| 7α-hydroxy-DHEA | | 1% |
| Phase B | | |
| Triethanolamine | | 0.25% |
| Preserving agent | | 0.2% |
| Glycerol | | 5% |
| Distilled water | qs | 100% |
| Phase C | | |
| Carbomer | | 0.3% |
| Distilled water | | 14.95% |
| Sodium hydroxide at 10% in water | | 0.25% |

The procedure is the same as that of Example 4. When combined with 7α-hydroxy-DHEA, isopropyl N-lauroyl sarcosinate allows the 7α-hydroxy-DHEA to avoid recrystallizing.

Example 7

Oil-in-water emulsion of oleosome type containing 1% 3β-acetoxy-7-oxo-DHEA

| | | |
|---|---|---|
| Phase A | | |
| Glyceryl stearate | | 2.5% |
| PEG-8 stearate | | 2.5% |
| Stearic acid | | 1% |
| Preserving agent | | 0.1% |
| Isopropyl N-lauroyl sarcosinate | | 8% |
| Miglyol 812 | | 22% |
| 3β-acetoxy-7-oxo-DHEA | | 1% |

-continued

| | | |
|---|---|---|
| Phase B | | |
| Triethanolamine | | 0.25% |
| Preserving agent | | 0.2% |
| Glycerol | | 5% |
| Distilled water | qs | 100% |
| Phase C | | |
| Carbomer | | 0.3% |
| Distilled water | | 14.95% |
| Sodium hydroxide at 10% in water | | 0.25% |

The procedure is the same as that of Example 4. When combined with 3β-acetoxy-7-oxo-DHEA, isopropyl N-lauroyl sarcosinate allows the 3β-acetoxy-7-oxo-DHEA to avoid recrystallizing.

The invention claimed is:

1. Cosmetic or dermatological composition comprising, in a physiologically acceptable medium containing at least one oil selected from the group consisting of (a) a hydrocarbon-based oil of plant, (b) a synthetic ester of a fatty acid of formula $R^6COOR^7$, wherein $R^6$ represents a fatty acid residue of 8-29 carbon atoms and $R^7$ represents a branched or unbranched hydrocarbon chain containing 3 to 30 carbon atoms, (c) a linear or branched hydrocarbon of mineral or synthetic origin, and (d) a silicone oil;

at least one of 5-n-octanoyl salicylic acid, a monovalent salt of 5-n-octanoyl salicylic acid and a divalent salt of 5-n-octanoyl salicylic acid, in an amount of between 0.001% and 15% by weight relative to the total weight of the composition; and isopropyl N-lauroyl sarcosinate of the formula $$CH_3—(CH_2)_{10}CO—N(CH_3)—CH_2—COO—CH—(CH_3)_2.$$

2. A method of manufacturing a dermatological composition comprising combining, in a physiologically acceptable medium, 5-n-octanoyl salicylic acid or a monovalent or divalent salt or mixtures thereof and isopropyl N-lauroyl sarcosinate.

3. A method of, caring for, cleansing or making up the skin, or caring for, cleansing or making up a mucous membrane, or caring for, cleansing or making up keratin fibers comprising applying a composition of claim 1 to said skin, mucous membrane or keratin fiber such that said skin, mucous membrane or keratin fiber is, cared for, cleansed or made up.

4. Cosmetic treatment process for combating the signs of ageing of skin or for improving the radiance of complexion of skin or for making facial skin smooth or for making body skin smooth or for treating wrinkles or fine lines of skin or for stimulating epidermal renewal or for depigmenting of skin or for bleaching skin, which process comprises applying to skin in need of any of said combating, improving, making, treating, stimulating, depigmenting or bleaching, a cosmetic composition according to claim 1, such that at least one of said ageing is combated, said radiance is improved, said facial skin is smoothed, said body skin is smoothed, said wrinkles or fine lines are treated, said epidermal renewal is stimulated, said skin is depigmented, or said skin is bleached.

5. The composition of claim 1 wherein said hydrocarbon-based oil of plant origin is selected from the group consisting of sunflower oil, corn oil, soybean oil, marrow oil, grapeseed oil, sesame oil, hazelnut oil, apricot oil, macadamia oil, arara oil, sunflower oil, castor oil, avocado oil, caprylic/capric acid triglycerides, jojoba oil and karite butter oil.

6. The composition of claim 1 wherein said synthetic ester is selected from the group consisting of purcellin oil, isononyl isononanoate, isopropyl myristate, 2-ethylhexyl palmitate, 2-octyldodecyl stearate, 2-octyldodecyl erucate, isostearyl isostearate, isostearyl lactate, octyl hydroxystearate, octyldodecyl hydroxystearate, diisostearyl malate, triisocetyl citrate, a fatty alkyl heptanoate, a fatty alkyl octanoate, a fatty alkyl decanoates, propylene glycol dioctanoate, neopentyl glycol diheptanoate, diethylene glycol diisononanoate, and pentaerythrityl tetraisostearate.

7. The composition of claim 1 wherein said linear or branched hydrocarbon of mineral or synthetic origin is selected from the group consisting of a volatile liquid paraffin, a non-volatile liquid paraffin, petroleum jelly, a polydecene, and a hydrogenated polyisobutene.

8. The composition of claim 1 wherein said silicone oil is selected from the group consisting of a cyclopolydimethylsiloxane, a polydimethylsiloxane comprising alkyl, alkoxy or phenyl groups, that are pendent or at the end of a silicone chain which contain from 2 to 24 carbon atoms, a phenyltrimethicone, a phenyldimethicone, a phenyltrimethylsiloxydiphenylsiloxane, a diphenyldimethicone, a diphenylmethyldiphenyltrisiloxane, a 2-phenylethyltrimethylsiloxysilicate and a polymethylphenylsiloxane.

* * * * *